United States Patent [19]

Karol et al.

[11] 4,115,425

[45] Sep. 19, 1978

[54] CYCLOPENTADIENYL CHROMIUM OXIDES

[75] Inventors: Frederick John Karol, Belle Mead, N.J.; Chisung Wu, Beaconsfield, Canada; Walter Thomas Reichle, Warren; Norma Jean Maraschin, South Bound Brook, both of N.J.

[73] Assignee: Union Carbide Corporation, New York, N.Y.

[21] Appl. No.: 779,690

[22] Filed: Mar. 21, 1977

[51] Int. Cl.$^2$ .............................................. C07F 11/00
[52] U.S. Cl. ........................ 260/438.5 R; 252/431 R; 526/126; 260/429 CY; 260/683.15 D; 526/127
[58] Field of Search ................ 260/438.5 R, 429 CY

[56] References Cited

U.S. PATENT DOCUMENTS

| 2,818,416 | 12/1957 | Brown et al. ................ 260/429 CY |
| 3,218,265 | 11/1965 | Rink et al. ................ 260/438.5 R X |

OTHER PUBLICATIONS

Karol et al., J. Polym. Sci. Part A-1, 10, 2621-2630, (1972).

*Primary Examiner*—Helen M. S. Sneed
*Attorney, Agent, or Firm*—Bernard Francis Crowe

[57] ABSTRACT

Cyclopentadienyl chromium alkyl/aryl oxides and siloxides have been synthesized which when deposited on silica and treated with a silane show catalytic activity in the polymerization of ethylene. These chromium compounds also can be used for scavenging oxygen and volatile sulfur compounds from various liquid and gaseous streams.

8 Claims, No Drawings

CYCLOPENTADIENYL CHROMIUM OXIDES

BACKGROUND OF THE INVENTION

This invention pertains to cyclopentadienyl chromium alkyl/aryl oxides and siloxides and more particularly to olefin polymerization catalysts prepared by depositing these oxides or siloxides on a silica support followed by treatment with a silane.

An object of this invention is to provide a description and method for the preparation of novel cyclopentadienyl chromium alkyl/aryl oxides and siloxides.

Another object is to provide a method for the polymerization of ethylene when these oxides or siloxides are deposited on silica supports and activated with silane compounds.

Another object is to provide scavengers for removing oxygen and volatile sulfur compounds from liquid and gaseous streams containing same.

Other objects will become apparent to those skilled in the art upon a reading of the specification.

SUMMARY OF THE INVENTION

Novel catalyst compositions for the polymerization of ethylene are provided by depositing an effective amount of cyclopentadienyl chromium alkyl/aryl oxides or siloxides, broadly referred to as cyclopentadienyl chromium oxides, having the formula:

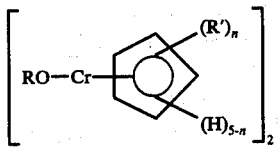

wherein $n$ is an integer having values of 0 to 5, R' is alkyl having 1 to 10 carbon atoms and R is a monovalent sterically hindered radical selected from the group consisting of

  (1)

wherein each of Y, Y' and Y" is alkyl having 1 to 18 carbon atoms or aryl having 6 to 12 carbon atoms,

  (2)

wherein Y, Y' and Y" are as defined above, and

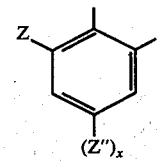  (3)

wherein Z and Z' are secondary or tertiary alkyls containing 3 to 5 carbon atoms, Z" is an alkyl group containing 1 to 6 carbon atoms and $x$ is an integer having values of 0 to 1, on a dried silica support together with at least one silane having the structure:

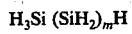

or

wherein $m$ is an integer having values of 0 to 3, R' is a saturated or unsaturated hydrocarbon having 1 to 10 carbon atoms and $p$ is an integer having values of 1 to 4 where the mole ratio of cyclopentadienyl chromium oxide:silane is in the range of about 1:0.5 to about 1:50, and the preferred range is about 1:2 to about 1:20. The amount of cyclopentadienyl chromium oxides deposited on the dried silica is not critical and can range from about 1 to about 50% by weight based on the weight of silica.

It was unexpected that the cyclopentadienyl chromium alkyl/aryl oxides or siloxides of this invention do not catalyze the polymerization of ethylene when used alone or when deposited on a silica support. It is only when the silica supported cyclopentadienyl chromium oxides are further treated with silanes that an active ethylene polymerization catalyst is obtained.

A further facet of this invention is the utility of the novel cyclopentadienyl chromium alkyl/aryl oxides or siloxides as scavengers of oxygen and volatile sulfur compounds from gas or liquid mixtures containing same. The method of contacting these compounds with such gas mixtures is not critical. Thus one may use these compounds as such or on inert supports in static or dynamic systems.

The cyclopentadienyl chromium oxides of this invention can be prepared by the interaction of chromocene, i.e., bis(cyclopentadienyl)chromium II with an appropriate alcohol. This is illustrated in the equation below:

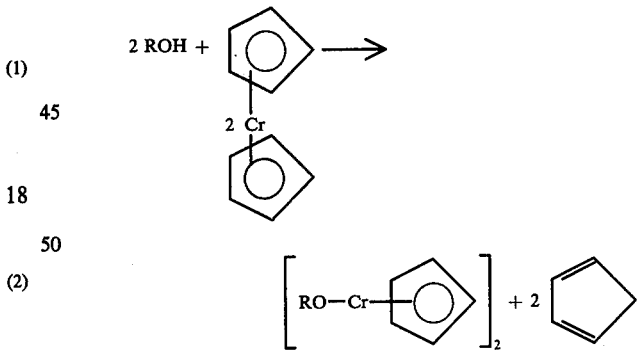

wherein R is a monovalent sterically hindered radical. Preferred alcohols for use in this preparation include alkanols, such as, t-butanol, t-pentanol, t-hexanol, and the like; silanols, such as, tri-t-butyl silanol, triphenyl silanol, tri-tolyl silanol, and the like; and substituted phenols, such as, 2,6-di-t-butylphenol, 2,6-di-t-butyl-p-cresol, 2,4-dimethyl-6-t-butylphenol, and the like.

The silicas which may be used as a support in the catalyst composition of the present invention are porous materials having a high surface area, that is, a surface area in the range of about 50 to about 1000 square meters per gram, and a particle size of about 25 to about 200 microns.

Any grade of silica can be used but microspheroidal intermediate density (MSID) silica having a surface area of about 350 square meters per gram and a pore diameter of about 200 angstroms (G-952 grade of W. R. Grace and Co.), and intermediate density (ID) silica having a surface area of 285 square meters per gram and a pore diameter of 164 angstroms (G-56 grade of W. R. Grace and Co.) are preferred. Other grades such as the G-968 silica (as designated by W. R. Grace and Co.), have a surface area of 700 square meters per gram and a pore diameter of 50–70 angstroms and are satisfactory.

Drying of the silica supports can be accomplished at nearly any temperature up to about its sintering for a period of time which is at least sufficient to remove the absorbed water from the support while at the same time avoiding such heating as will remove all of the chemically bound water from the support. The passage of a stream of dry inert gas through the support during the drying aids in the displacement of water from the support. Drying temperatures of from about 150° to about 1000° C. for about 6 hours or so is sufficient if a well-dried inert gas is used.

In the silane compounds which can be used to prepare the ethylene polymerization catalysts of this invention having the formula:

$$R'_{4-p} Si H_p$$

R' can be alkyl, alkenyl, aryl, aralkyl, cycloalkyl, or alkaryl groups, such as, methyl, ethyl, n-propyl, isopropyl, n-butyl, heptyl, hexyl, cycloheptyl, allyl, propenyl, phenyl, naphthyl, benzyl and the like. Specific examples of these derivatives are diphenyl silane, triphenyl silane, di-1-naphthyl silane, phenylsilane, ethyl silane, diethyl silane, triethyl silane, methyl diethyl silane, triisopropyl silane, tri(n-propyl) silane, diphenylmethyl silane, dibenzyl silane, triallyl silane, tri(n-hexyl) silane, tribenzyl silane, trimethyl silane, tributyl silane, and the like.

Silane compounds having the formula:

$$H_3Si (SiH_2)_m H$$

include silane ($SiH_4$), the unsubstituted dimer, trimer and tetramer of silane, and substituted derivatives of silane.

Supported cyclopentadienyl chromium oxide can be prepared by a slurry technique where the solution containing the cyclopentadienyl chromium oxide and solvent is added under conditions which exclude the presence of air and moisture to a slurry of the dried silica support and a solvent. The slurry may be stirred for a period of up to about 4 hours to obtain good absorption of the oxide on the support. The solvent is then drained from the slurry or the retained solvent can be evaporated under conditions which exclude oxygen and moisture to yield a dry, powdery silica supported oxide. To prepare the ethylene polymerization catalysts, the silica supported oxides obtained as above are mixed with the silanes described previously in a ratio of about 0.1 to 40 weight percent of silane to about 60 to 99.9 percent of supported oxides. About 0.5 to about 50 moles of silane are used per mole of supported oxide. The silane may be added to the supported oxide prior to the ethylene polymerization reaction or the two components of the catalyst may be separately added to the polymerization system. The silane may be added to the silica support before, after, or concurrently with the addition of the cyclopentadienyl chromium oxide to the silica support.

When the silane is added to the silica supported cyclopentadienyl oxide, the silane is conveniently deposited from a suitable inert solvent, such as, those used in the polymerization reaction. Suitable inert solvents include saturated aliphatic hydrocarbons, such as, pentane, hexane, heptane, isooctane, purified kerosene and the like; aromatic hydrocarbons, such as, benzene, toluene, xylene, and the like. Particularly preferred solvents are cyclohexane, pentane, hexane and heptane.

The invention is further described in the Examples which follow. All parts and percentages are by weight unless otherwise specified.

EXAMPLE 1 — PREPARATION OF CYCLOPENTADIENYL CHROMIUM OXIDES

A. Reaction of Triphenylsilanol with Chromocene

Into a 100 ml round-bottom flask fitted with nitrogen inlet and outlet tubes was charged 1.82 g. (0.01 mole) of chromocene, i.e., bis(cyclopentadienyl)chromium, 2.76 g. (0.01 mole) of triphenylsilanol and 15 ml. of toluene under nitrogen. The reaction mixture was refluxed for 5 hours during which time a dark purple solution was obtained. Evaporation of toluene afforded a cyclopentadienyl chromium compound having the empirical formula:

$$[(C_6H_5)_3SiO\ Cr\ C_5H_5]_2$$

This is a dark purple solid which resisted sublimation at 200° C./0.2 mm Hg. The ultraviolet absorption spectrum of this product dissolved in n-hexane showed an absorption peak, $\lambda_{max} = 545\ m\mu$.

Elemental analyses for C and H are presented below: Found: %C, 69.83; %H, 5.21. Calculated: %C, 70.40, %H, 5.10.

B. Reaction of t-Butanol with Chromocene

To a solution of chromocene (27.1 millimoles in 20 ml of toluene) was added 32.5 millimoles of dry t-butanol and the mixture refluxed for 4 hours. The volatiles were then removed under vacuum. The residue was sublimed at 110° C./0.001 mm Hg affording 4.08 g. (79% yield) of dark red crystals having a melting point of 117°–119° C. Crystallization from pentane (3 times at −70° C.) yielded dark red crystals having a melting point of 120°–121° C. Molecular weights of 365 and 370 determined crysoscopically in benzene at a concentration of 0.5% by weight are consistent with an empirical formula of:

$$[C_5H_5Cr\ OC(CH_3)_3]_2$$

Elemental analyses are presented below: Found: %C, 55.65; %H, 7.36; %Cr, 27.50. Calculated: %C, 56.86; %H, 7.37; %Cr, 27.35.

The calculated molecular weight is 380.

C. Reaction of 2,6-Ditertiarybutyl Phenol with Chromocene

To a solution of 12.1 millimoles of chromocene in 20 ml. of toluene was added 12.7 millimoles of 2,6-ditertiarybutyl phenol. This mixture was refluxed for 18 hours. The brown solution was pumped dry. The solid residue was sublimed at 60° C./0.1 mm Hg yielding 3.4 g. of blue crystals.

Elemental analyses for C and H are presented below: Found: %C, 71.05; %H, 8.21; %Cr, 17.0. Calculated: %C, 70.81; %H, 8.07; %Cr, 16.15.

These analyses are consistent with the empirical formula:

[(CH₃)₆C₂C₆H₃OCr C₅H₅]₂ of 4.8 dg./min. and a high load melt index of 207 dg./min. Melt index measurements were made in conformity with ASTM D-1238, Condition E.

These data are collated in Table 1 together with data obtained from two additional experiments using the cyclopentadienyl chromium oxide prepared in Example 1C from 2,6-ditertiarybutyl phenol and chromocene.

TABLE 1

Ethylene Polymerization Studies With Cyclopentadienyl Chromium Oxide Catalysts

| Run No. | Oxide Identity | Catalyst Amount in Millimoles | Silica Supports Type | Wt. In. | Butylsilane /Cr Molar Ratio | H₂ psig | Ethylene psig | Temp. °C. | Time Min. | Yield G. | MI$^{(a)}$ dg./min. | HLMI$^{(b)}$ dg./min |
|---|---|---|---|---|---|---|---|---|---|---|---|---|
| 1 | [(C₆H₅)₃SiOCrC₅H₅]₂ | 0.53 | 952-800 | 2 | 4 | 40 | 360 | 91 | 55 | 138 | 4.8 | 207 |
| 2 | [(CH₃)₆C₂C₆H₃OCrC₅H₅]₂ | 0.11 | 952-600 | 0.4 | 4.0 | 20 | 180 | 79 | 90 | 52 | 11.6 | — |
| 3 | " | 0.28 | 952-600 | 0.4 | 4.8 | 25 | 175 | 84 | 120 | 158 | 45 | — |

$^{(a)}$Melt index.
$^{(b)}$High load melt index.

EXAMPLE 2 — ETHYLENE POLYMERIZATION AND CATALYST PREPARATION

One hundred ml. of n-hexane dried with activated molecular sieves (Linde 5A) prior to use was added to an 8 ounce serum-capped bottle and purged with argon for 30 minutes. Grade 952 silica obtained from Davison Chemicals Division of W. R. Grace and Co. was dried by heating at 800° C. for 16 hours in an inert atmosphere of nitrogen. To the serum-capped bottle was added 2 grams of this dried silica through a small hole in the cap. A second serum cap was fitted over the first to prevent contamination by air and water. After purging the contents in the bottle for 15 minutes, a solution of 0.53 millimoles of the compound prepared in Example 1A (from triphenylsilanol and chromocene) in toluene was added by hypodermic syringe. The contents of the bottle were rapidly agitated by a magnetic stirring bar for thirty minutes during which time complete deposition of the oxide on the silica support took place. Then 2 millimoles of butyl silane in 0.5 ml of n-hexane was added by hypodermic syringe to the bottle. The resultant mixture was charged to a 1-liter chrome-plated stainless steel autoclave, equipped with a pressure gauge, appropriate argon and ethylene inlets and outlets, and a propellor stirring blade for agitation. The catalyst was suspended in the n-hexane diluent by agitation. The autoclave was flushed with argon and pressurized with 40 psig of hydrogen. Then a constant pressure of ethylene of 360 psig was maintained in the autoclave. The flow rate of ethylene was observed by means of a high pressure rotameter in the ethylene feed line. Control of reaction exotherm was maintained by means of a cold water circulating through the autoclave jacket. In this manner a temperature of 91° C. was maintained for 55 minutes. Polymerization was terminated and a yield of 138 g. of polyethylene recovered having a melt index

EXAMPLE 3 — ETHYLENE POLYMERIZATIONS

Using the polymerization catalyst preparation described in Example 2 with 0.4 g. of Grade 56 silica dehydrated at 600° C. with varying amounts of the oxides prepared from t-butanol/chromocene, triphenylsilanol/chromocene and 2,6-ditertiarybutyl phenol/chromocene and butyl or pentyl silanes, several catalysts were prepared and evaluated for the polymerization of ethylene. The polymerization conditions were a temperature of 89° C., a hydrogen/ethylene ratio of 0.05–0.13 and an ethylene pressure of 200 psig using the equipment and procedure outlined in Example 2. The yields of polyethylene obtained are recorded in Table 2 together with a Control A where no silane was used in preparing a catalyst from t-butanol and chromocene.

TABLE 2

Ethylene Polymerization Studies With Cyclopentadienyl Chromium Oxide Catalysts

| Run No. | Oxide Catalyst Type | Millimoles | Silane Compound Type | Millimoles | Polyethylene Yield Grams |
|---|---|---|---|---|---|
| Control A | [(CH₃)₃COCrC₅H₅]₂ | 0.21 | None | None | 0 |
| 4 | " | 0.11 | CH₃(CH₂)₄SiH₃ | 0.50 | 176 |
| 5 | " | 0.11 | " | 0.92 | 133 |
| 6 | [(C₆H₅)₃SiOCrC₅H₅]₂ | 0.53 | CH₃(CH₂)₃SiH₃ | 7.7 | 138 |
| 7 | [(CH₃)₆C₂C₆H₃OCrC₅H₅]₂ | 0.11 | CH₃(CH₂)₄SiH₃ | 0.44 | 52 |

EXAMPLE 4 — OXYGEN SCAVENGING BY A CYCLOPENTADIENYL CHROMIUM OXIDE 0.16 millimoles (30 mg.) of cyclopentadienyl chromium oxide (prepared as in Example 1B from chromocene and t-butanol) solid was dissolved in 38 ml. of distilled, N₂ purged toluene. This procedure was done in a dry box to exclude air and moisture. The solution of cyclopentadienyl chromium oxide in toluene was contained in a serum capped 6 oz. glass bottle. The solution was dark purple.

The serum capped bottle was removed from the dry box and pure oxygen was bubbled through the solution by passing the oxygen through a hypodermic needle which pierced the serum cap. Another needle provided a vent for the pressure. After 15 min. of O₂ bubbling, the solution had turned dark green. Upon removing the serum cap and exposing the solution to the air no further change in color was noticed.

The color change of the solution, from dark purple to dark green indicates that oxygen has reacted with the cyclopentadienyl chromium oxide in the solution, and was effectively removed from the gas stream.

Although the invention has been described with a certain degree of particularity, it is understood that the present disclosure of the preferred forms has been made only by way of example and that numerous changes may be resorted to without departing from the spirit and scope of the invention.

What is claimed is:

1. Cyclopentadienyl chromium alkyl/aryl oxides or siloxides having the formula:

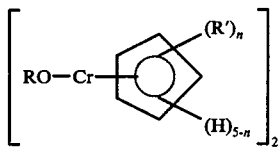

wherein $n$ is an integer having values of 0 to 5, R' is alkyl having 1 to 10 carbons and R is a monovalent sterically hindered radical selected from the group consisting of:

 (1)

wherein each of Y, Y' and Y" is alkyl having 1 to 18 carbons or aryl having 6 to 12 carbons,

 (2)

wherein Y, Y' and Y" are as defined above, and

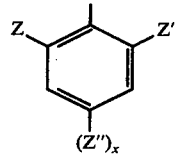 (3)

wherein Z and Z' are secondary or tertiary alkyls containing 3 to 5 carbon atoms, Z" is an alkyl group containing 1 to 6 carbon atoms and $x$ is an integer having values of 0 to 1.

2. Cyclopentadienyl chromium alkyl/aryl oxides claimed in claim 1 wherein R is

3. Cyclopentadienyl chromium alkyl/aryl oxides claimed in claim 2 wherein each of Y, Y' and Y" is methyl.

4. Cyclopentadienyl chromium siloxide claimed in claim 1 wherein R is

5. Cyclopentadienyl chromium siloxide claimed in claim 4 wherein each of Y, Y' and Y" is phenyl.

6. Cyclopentadienyl chromium alkyl/aryl oxide claimed in claim 1 wherein R is

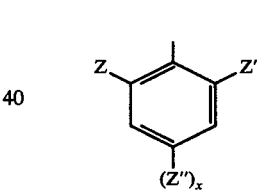

7. Cyclopentadienyl chromium alkyl/aryl oxide claimed in claim 6 wherein Z and Z' are each t-butyl and $x = 0$.

8. Cyclopentadienyl chromium alkyl/aryl oxide claimed in claim 6 wherein Z and Z' are each t-butyl, Z" is methyl and $x = 1$.

* * * * *